US00PP11877P2

(12) United States Plant Patent
Law

(10) Patent No.: US PP11,877 P2
(45) Date of Patent: May 15, 2001

(54) POINSETTIA PLANT NAMED 'ECKADAMA'

(75) Inventor: Robert Law, Crestline, OH (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/345,564

(22) Filed: Jun. 30, 1999

(51) Int. Cl.[7] ..... A01H 5/00
(52) U.S. Cl. ..... Plt./306
(58) Field of Search ..... Plt./306, 303, 307

(56) References Cited

PUBLICATIONS

UPOV–ROM GTIM Computer Database 2000/02, GTI Jouve Retrieval Software, citation for 'Eckadama', Mar. 1998.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eckadama', characterized by its bright coral pink bracts; dark green leaves; compact, upright and spreading plant habit; very freely branching habit; early flowering; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckadama'.

The new Poinsettia is a naturally-occuring mutation of the commercial *Euphorbia pulcherrima* Willd. cultivar '490', disclosed in U.S. Plant Pat. No. 7,825. The new Poinsettia was selected by the Inventor in a greenhouse in Crestline, Ohio, in 1994.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be unique characteristics of 'Eckadama'. These characteristics in combination distinguish 'Eckadama' as a new and distinct cultivar:

1. Bright coral pink bracts.
2. Dark green leaves.
3. Compact, upright and spreading plant habit.
4. Very freely branching habit.
5. Early flowering.
6. Excellent postproduction longevity.

In side-by-side comparisons conducted in Encinitas, Calif., plants of the new Poinsettia differed from plants of the parent cultivar, '490', primarily in bract coloration as bracts of '490' are red.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph on the first sheet comprises a side perspective view of a typical plant of 'Eckadama'.

The photograph at the top of the second sheet comprises a top perspective view of a typical plant of 'Eckadama'.

The photograph at the bottom of the second sheet is a close-up view of typical bracts and leaves of 'Eckadama' (left) and '490' (right).

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a polyethylene-covered greenhouse with day temperatures about 22 to 24° C., night temperatures about 16 to 18° C., and light levels about 4,000 foot-candles. Plants were grown in 16.5-cm pots, pinched one time, and flowered under naturally lengthening nights during the fall/early winter.

In the following description, color references are made to The Royal Horticultural Society Colour Chart except where general terms of ordinary dictionary significance are used.

Botanical classification: *Euphorbia pulcherrima* Willd. 'Eckadama'.

Parentage: Naturally-occuring mutation of *Euphorbia pulcherrima* Willd. cultivar '490', disclosed in U.S. Plant Pat. No. 7,825.

Propagation:

*Type cutting.*—Terminal cuttings.

*Time to initiate roots.*—Summer: About 12 to 18 days at 26 to 28° C. Winter: About 15 to 18 days at 24° C.

*Time to develop roots.*—Summer: About 26 days at 26 to 28° C. Winter: About 26 days at 24° C.

*Rooting habit.*—Thick, freely branching, becoming fibrous with development.

Plant description:

*Plant form.*—Inverted triangle, top of plant rounded.

*Growth habit.*—Compact, upright and spreading. Very freely branching. Branching is enhanced by removing the shoot apex.

*Plant vigor.*—Moderate to high.

*Plant height.*—About 24 cm.

*Crop time.*—From unrooted cuttings to a flowering plant in a 16.5-cm container, about 16 weeks are required.

*Stem description.*—Number of lateral branches: About seven lateral branches are formed after removal of the terminal apex. Lateral branch length: About 16.5 cm. Internode length: About 7.5 mm. Stem color: 146B.

*Foliage description.*—Quantity of leaves per lateral branch: About 12. Length: About 12 cm. Width: About 7.5 cm. Shape: Mostly ovate, occasionally lobed. Apex: Acuminate. Base: Acute. Margin: Entire. Texture: Smooth; dull. Mostly glabrous with very slight pubescence on lower surface. Color: Young foliage, upper surface: Darker than 147A. Young foliage, lower surface: 147A to 147B. Mature foliage, upper surface: Darker than 147A. Mature foliage, lower surface: 147A to 147B. Venation, upper surface: 147C. Venation, lower surface: 147B to 147C. Petiole: Length: About 5 cm. Diameter: About 2.5 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Early flowering, response time is about 8 weeks.

*Quantity of inflorescences.*—One per lateral branch, usually about seven per plant.

*Inflorescence size.*—Diameter: About 29 cm. Height (depth): About 4.5 cm.

*Flower bracts.*—Quantity of flower bracts per inflorescence: Usually about 12 primary bracts and about 6 smaller secondary bracts per inflorescence. Length, largest bracts: About 15 cm. Width, largest bracts: About 11 cm. Shape: Mostly ovate, occasionally lobed. Apex: Acuminate. Base: Acute. Margin: Entire. Texture: Smooth. Aspect: Mostly flat. Color: Developing, upper surface: More rose and not as gray as 53B. Developing, lower surface: 53B. Mature, upper surface: Slightly brighter than 50A; fading to 50B with subsequent development. Mature, lower surface: 47B.

*Cyathia.*—Quantity: Usually about 10 per corymb. Diameter of cyathia cluster: About 2 by 2.5 cm. Length: About 1.4 cm. Width: About 4 mm. Color: Immature: 144A. Mature: 144A to 144B. Peduncle: Length: About 4 mm. Aspect: Strong, erect. Color: 144B. Stamens: Stamen number: Typically more than 10 per cyathium. Anther size: Less than 1 mm. Anther shape: Oval. Anther color: 26B. Amount of pollen: Scarce to moderate. Pollen color: 7A. Pistils: No pistillate flowers observed. Nectary color: 14A.

Disease resistance: No fungal, bacterial nor viral problems observed on plants grown under commercial conditions.

Postproduction longevity: Generally plants maintain good substance and bract color for about eight weeks under interior conditions.

It is claimed:

1. A new and distinct cultivar of Poinsettia plant named 'Eckadama', as illustrated and described.

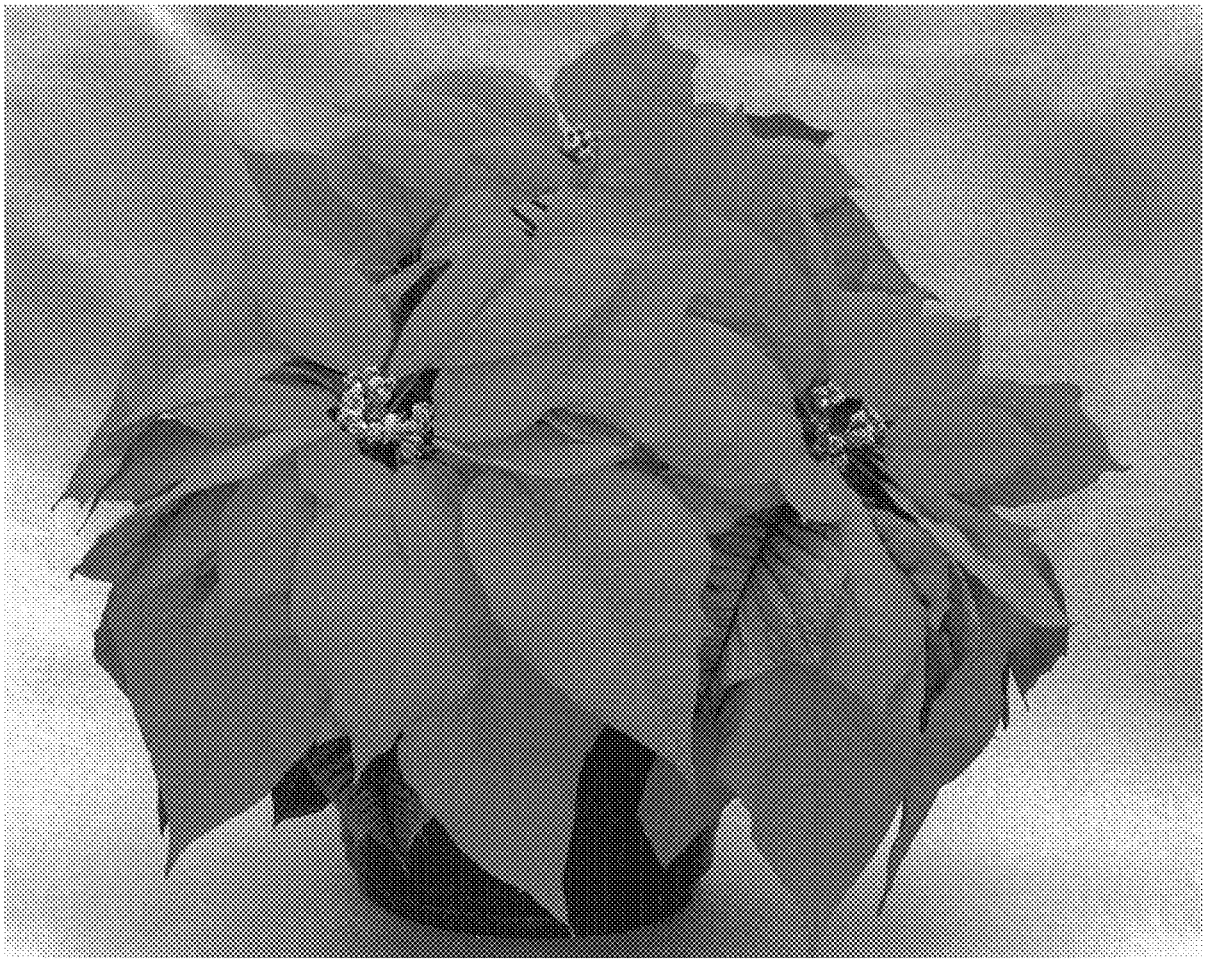

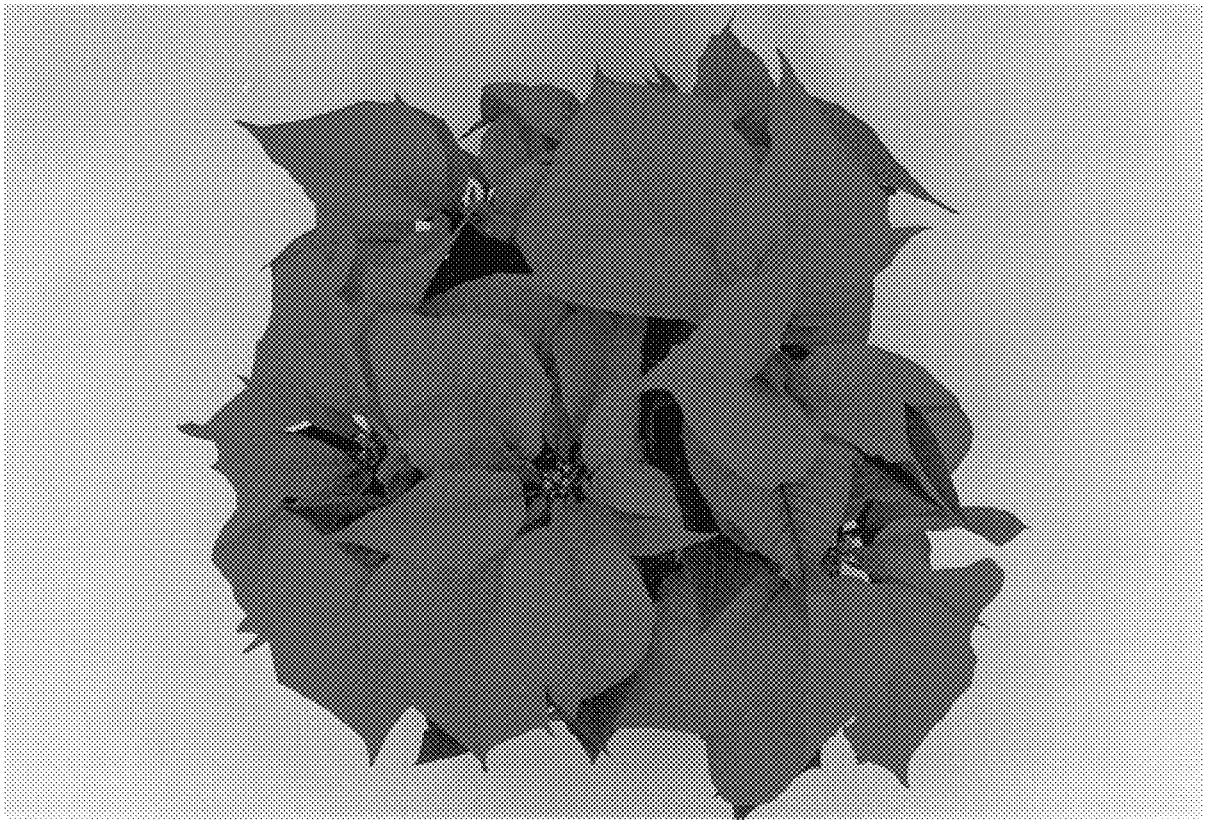
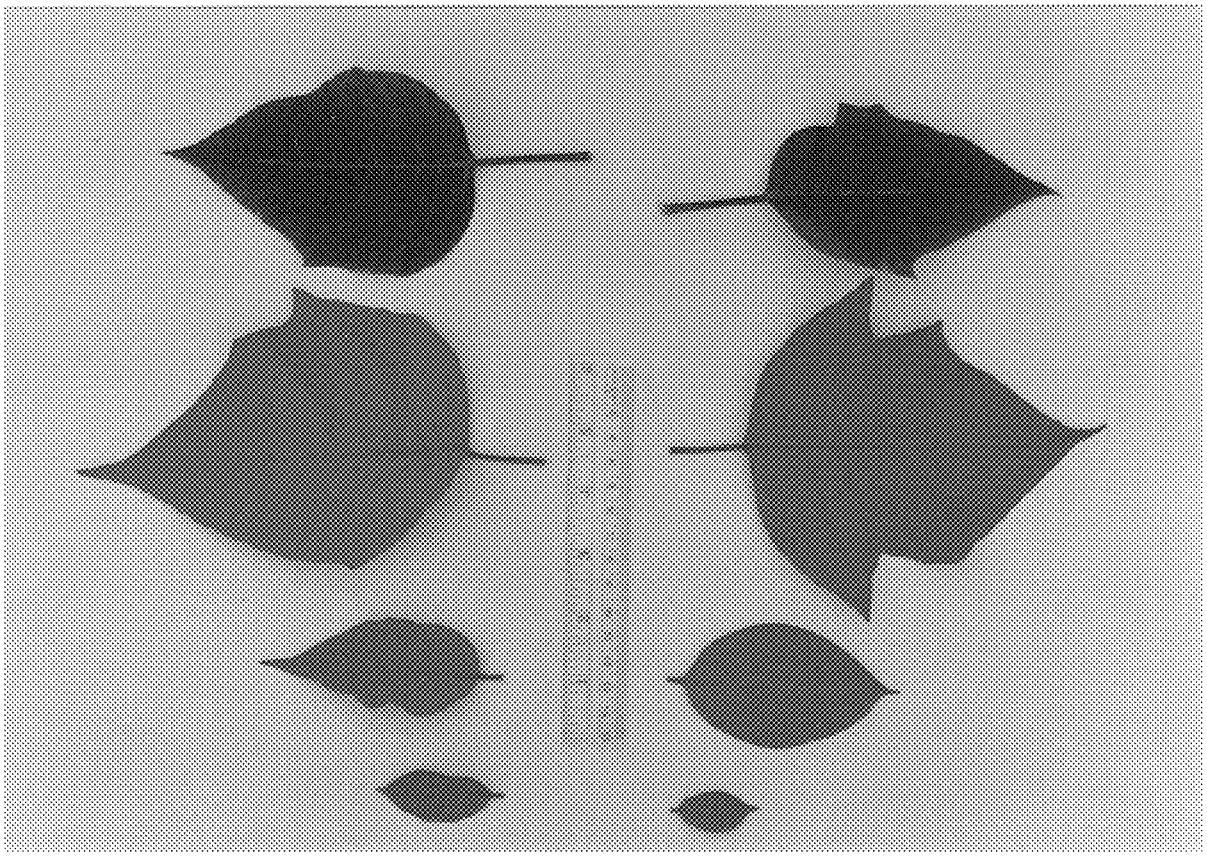

* * * * *